United States Patent [19]
Bugle et al.

[11] Patent Number: 5,246,530
[45] Date of Patent: Sep. 21, 1993

[54] METHOD OF PRODUCING POROUS METAL SURFACE

[75] Inventors: Clifford M. Bugle, Library; Alfred L. Donlevy, Pittsburgh, both of Pa.

[73] Assignee: Dynamet Incorporated, Washington, Pa.

[21] Appl. No.: 844,955

[22] Filed: Feb. 28, 1992

Related U.S. Application Data

[63] Continuation-in-part of Ser. No. 511,554, Apr. 20, 1990, abandoned.

[51] Int. Cl.$^5$ ............................. B44C 1/22; C23F 1/00
[52] U.S. Cl. .................................. 156/643; 156/645; 156/651; 156/659.1; 156/667; 156/345; 219/121.69
[58] Field of Search ............... 156/643, 651, 654, 656, 156/659.1, 664, 645, 634, 667, 345; 623/1, 16, 18, 22, 23; 219/121.68, 121.69, 121.85

[56] References Cited

U.S. PATENT DOCUMENTS

| | | | |
|---|---|---|---|
| 3,867,217 | 2/1975 | Maggs et al. | 156/643 |
| 4,608,052 | 8/1986 | Van Kampen et al. | 623/22 |
| 4,612,160 | 9/1986 | Donlevy et al. | 419/2 |
| 4,673,409 | 6/1987 | Van Kampen | 623/23 |
| 4,729,766 | 3/1988 | Bergentz et al. | 623/1 |
| 4,778,469 | 10/1988 | Lin et al. | 623/16 |
| 4,795,472 | 1/1989 | Crowninshield et al. | 623/23 |
| 4,801,300 | 1/1989 | Kurze et al. | 623/22 |
| 4,834,756 | 5/1989 | Kenna | 623/16 |
| 4,851,004 | 7/1989 | Homsy | 623/16 |
| 4,854,496 | 8/1989 | Bugle | 228/193 |
| 4,863,474 | 9/1989 | Brown et al. | 623/16 |
| 4,863,475 | 9/1989 | Andersen et al. | 623/16 |
| 4,865,604 | 9/1989 | Rogozinski | 623/18 |
| 4,883,491 | 11/1989 | Mallory et al. | 623/22 |
| 4,888,024 | 12/1989 | Powlan | 623/23 |
| 4,892,549 | 1/1990 | Figgie, III et al. | 623/22 |
| 4,892,552 | 1/1990 | Ainsworth et al. | 623/23 |

*Primary Examiner*—William A. Powell
*Attorney, Agent, or Firm*—Webb, Burden, Ziesenheim & Webb

[57] ABSTRACT

A porous surface is selectively formed on a workpiece such as a medical implant by pulsing a laser device in a controlled manner to produce a plurality of small, spaced-apart cavities of uniform or variable depth. The porous surface provides a mechanical grip with bone cement as well as a medium for bone and tissue ingrowth.

9 Claims, 12 Drawing Sheets

Laser drilled conical hole. 50X, Mt. 1127

Laser drilled bulbous hole. 50X, Mt. 1128

Laser drilled hole at 20° to the surface. 50X, Mt. 963.

Laser drilled hole at 45° to the surface. 50X, Mt. 959.

Laser roughened surface. 50X, Mt. 1593.

The left side of disk had BN coating. 1.5X.

Enlargement Of Figure 18 showing relatively clean surface on BN coated area (left side) as compared to splatter on non-coated area (right side). 10X.

Cross-section of laser processed disk from BN coated area. 100X. MT 1672

Cross-section of laser processed disk from non-coated area showing attached splatter. 100X MT 1672

METHOD OF PRODUCING POROUS METAL SURFACE

This is a continuation-in-part of copending application(s) Ser. No. 07/511,554 filed on Apr. 20, 1990, now abandoned.

BACKGROUND OF THE INVENTION

1. Field of the Invention

The present invention relates generally to porous metal surfaces and methods for forming such surfaces, particularly for use in medical prostheses.

2. Brief Description of the Prior Art

It is well-known in the medical implant art to provide a porous surface on selected areas on a medical prosthesis to permit the bone cement, or ideally the bone itself, to penetrate the voids in the surface in order to establish and maintain a strong mechanical bond with the implant. A frequently employed technique for creating such an active implant surface area involves the selective placement of a porous coating on the implant device. The most commonly used porous coatings are gravity or pressure sintered spherical powders, diffusion bonded metal fibers and plasma sprayed powder coatings. Exemplary of such sintered metal powder coatings are those described in our U.S. Pat. Nos. 4,612,160 and 4,854,496.

Titanium and titanium alloys have experienced wide usage as medical implant materials, especially for medical prostheses such as orthopedic devices in the form of knee and hip joints. Diffusion bonded metal fiber coatings have been produced from titanium wire in the form of random porous fiber metal coatings. Likewise, in plasma sprayed coatings, it is also known to utilize either commercially pure titanium or titanium alloy powders. The desirability of producing porous surfaces on medical prosthetic devices is well-known as seen, for example, in U.S. Pat. No. 3,855,638 to Pilliar, U.S. Pat. No. 3,605,123 to Hahn, U.S. Pat. No. 4,017,911 to Kafesjian and U.S. Pat. No. 3,808,606 to Tronzo.

The various medical factors involved in bone or tissue ingrowth, including those involved in bone cement adhesion, are documented and well-known to those in the medical implant art. The medical community has also clearly indicated that control of the pore size in porous coatings is highly desirable and that dimensional control of the implant itself is absolutely necessary for satisfactory prosthetic devices. In addition, careful control of the metal chemistry and the elimination of sources of contamination are also recognized to be essential for implanted prosthetic devices. As noted previously, it has been common practice to produce porous surfaces by applying a porous coating to the implant substrate. It has been found in some instances, however, that after prolonged periods of use, portions of the porous coating may break loose from the coating mass. When such an event occurs, the loose porous coating material becomes a contaminant in the surrounding tissue. Naturally, such contamination is highly objectionable since it may require surgical intervention in order to correct the problem.

It is certainly desirable to prevent such contamination while still providing sufficient porosity in the implant surface to permit proper mechanical interlocking by cement adhesion and bone or tissue ingrowth. The present invention solves these prior shortcomings by providing an improved porous surface which eliminates the opportunity for surface breakaway and subsequent tissue contamination. The present invention provides a process for forming a porous surface on or in a workpiece such as a medical implant, having closely controlled porosity which may be uniformly dispersed or varied in spacing and in size in pre-selected areas over the implant surface. The process of the present invention further provides a porous surface which is more economical to produce than comparable processes such as the commonly used powder metallurgy sintering or diffusion bonding processes of the prior art. The present invention also provides a medical implant device having extremely close dimensional tolerances with closely controlled porous surface areas having pores or cavities of selected size and spacing. The present invention provides a porous surface and process for producing same in which the size of each cavity with respect to its diameter and depth may be closely controlled in either a constant or varying pattern across the workpiece to provide consistent high quality surfaces. In addition, the cosmetic appearance of the porous surface is enhanced.

SUMMARY OF THE INVENTION

The present invention is directed to the formation of porous surfaces, wherein a workpiece of, for example, commercially pure titanium, titanium alloy, or cobalt-chromium alloy has a plurality of cavities formed therein of a predetermined diameter, depth and spacing. The method of the present invention comprises the steps of providing a workpiece, such as a medical implant device, for example; mounting the workpiece in a fixture, preferably having positioning means associated therewith; providing a laser in spaced relation to said mounted workpiece; adjusting the power of the laser to provide a laser beam of a selected value whereby a cavity of pre-selected depth is drilled into the surface of the workpiece; and pulsing the laser at a selected frequency while simultaneously moving one or both of the laser and workpiece relative to one another, whereby a plurality of spaced-apart cavities of a pre-selected size and spacing are formed in the workpiece surface. By selecting the proper focal point, laser power level and indexing location, a surface with selected surface connected porosity characteristics is produced. The porosity may be produced in specific locations, with a pre-selected size and density of cavities to provide a surface area of closely controlled dimensions particularly suitable for medical implant devices.

By varying the pulse duration and power level of the laser, cavities of selected geometry, such as conical or "bulbous" shapes are obtained. The bulbous cavity shape possesses a wider diameter beneath the surface of the workpiece than it does at the surface. After implant, the bone tissue can grow into these shaped cavities crating an improved mechanical interlock.

The present invention also contemplates laser drilling spaced apart cavities wherein the respective longitudinal center lines of the cavities are oriented at an angle relative to the surface of the workpiece. Such angularly oriented cavities enhance bone ingrowth and enable normal shear loading to include a compressive component.

The laser treated surfaces according to the present invention also provide a foundation for coating with suitable bone growth stimulants and medications. A roughened surfaced provided by the invention yields increased surface area for such coating to adhere. Such surfaces also protect the coatings from direct shear loads as would otherwise occur with a smooth surface.

In order to provide a clean, splatter free surface, i.e., free of frozen metal droplets, one aspect of the present invention includes the step of applying a thin coating of a release agent to the form of a refractory material to the surface of the workpiece prior to laser drilling. After drilling, the workpiece is easily and quickly cleaned to remove the release agent coating and the metal splatter. In a modified method, a chemical maskant in the form of an acid resistant coating, typically a polymer, is first applied to the workpiece and the aforementioned refractory release agent may be supplied as a coating over the chemical maskant. Cavities are then laser drilled into the workpiece. The drilled workpiece may then be subsequently etched electrolytically or in acid to enlarge or modify the shape of the cavities as well as to remove any metal splatter which might have fallen into the cavities during laser drilling. A workpiece having a porous surface produced in accordance with the present invention is also suitable for uses other than medical implants, such as, for example, titanium components bonded by epoxy to other structural elements. The porous surface provides an excellent base for obtaining a strong mechanical joint with castable epoxy materials.

BRIEF DESCRIPTION OF THE DRAWINGS

These, as well as other objects and advantages of the present invention, will become clearer when reference is made to the following description when taken with the drawings in which.

DETAILED DESCRIPTION OF THE INVENTION

It will be readily understood that the present invention utilizing a laser enables the production of medical implant devices of very close dimensional tolerances and without potential contamination since the conventional porous surface layer is eliminated. As is known, the term laser is an acronym for light amplification by stimulated emission of radiation. Further description of lasers may be found in Van Nostrand's Scientific Encyclopedia, Seventh Edition, Douglas M. Considine, Editor. There are a number of materials that are capable of being utilized as lasers, however, those which most often are used for industrial processing are either of the $CO_2$ or YAG type. Of particular usefulness in the present invention is the YAG laser utilizing a neodymium-doped yttrium aluminum garnet material operating at between about 25 to 50 watts of power. The power level is adjusted according to the size, depth, and repetition rate utilized for drilling into the surface layer of the implant substrate being treated.

According to the process of the present invention, the workpiece, such as a medical implant or other workpiece whose surface is to be modified, is positioned in the near focal point of a suitable laser system. The laser may be pulsed, for example, at between about 8 to about 15 pulses per second at the desired power level to produce a cavity of desired depth and diameter. Either the laser beam is moved to another selected position and pulsed again, or the substrate is moved prior to the next laser pulse. Those skilled in the art will readily understand that a combination of concurrent movement of the substrate and laser beam will accomplish the same end result. Indexing movement of the workpiece or laser device is either continuous or intermittent.

By selection of the focal point, laser power level and indexing parameters, a surface with any desirable porosity is easily produced and replicated with consistent quality. The porous surface formed by the present invention may be produced in specific locations on the workpiece and with a selected density of cavities. The porosity produced is easily distinguished from laser marking such as that utilized to mark metal and plastic items for identification or decorative purposes, as such marking is less than 0.005" deep. In order for porosity to be useful for either bone ingrowth or adhesive bonding, the depressions are significantly over 0.005" deep, and preferably on the order of about 0.030" deep.

Perhaps the greatest advantage of the present invention over prior art methods resides in the fact that the porous surface is integral with the implant base material so as to avoid the flaking contamination problems present in prior coatings applied by sintering, plasma spraying, or by diffusion bonding techniques.

Figure 1:
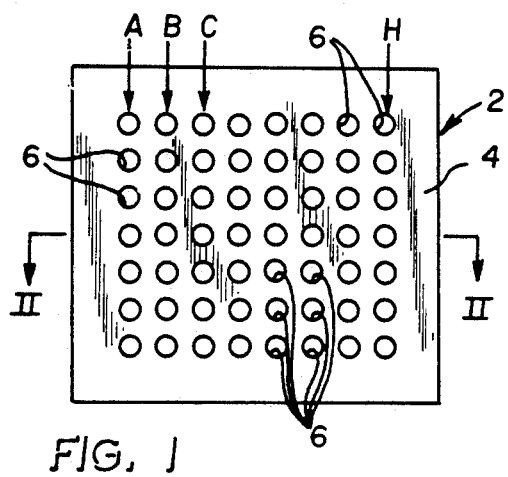
FIG. 1 is an enlarged plan view of a porous surface in accordance with the present invention.
Figure 2:
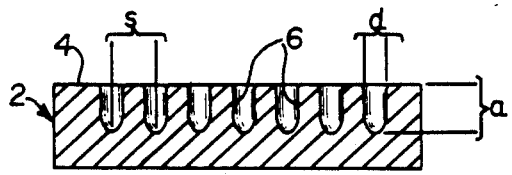
FIG. 2 is a side cross-sectional view taken along line II—II of FIG. 1.
Figure 7:
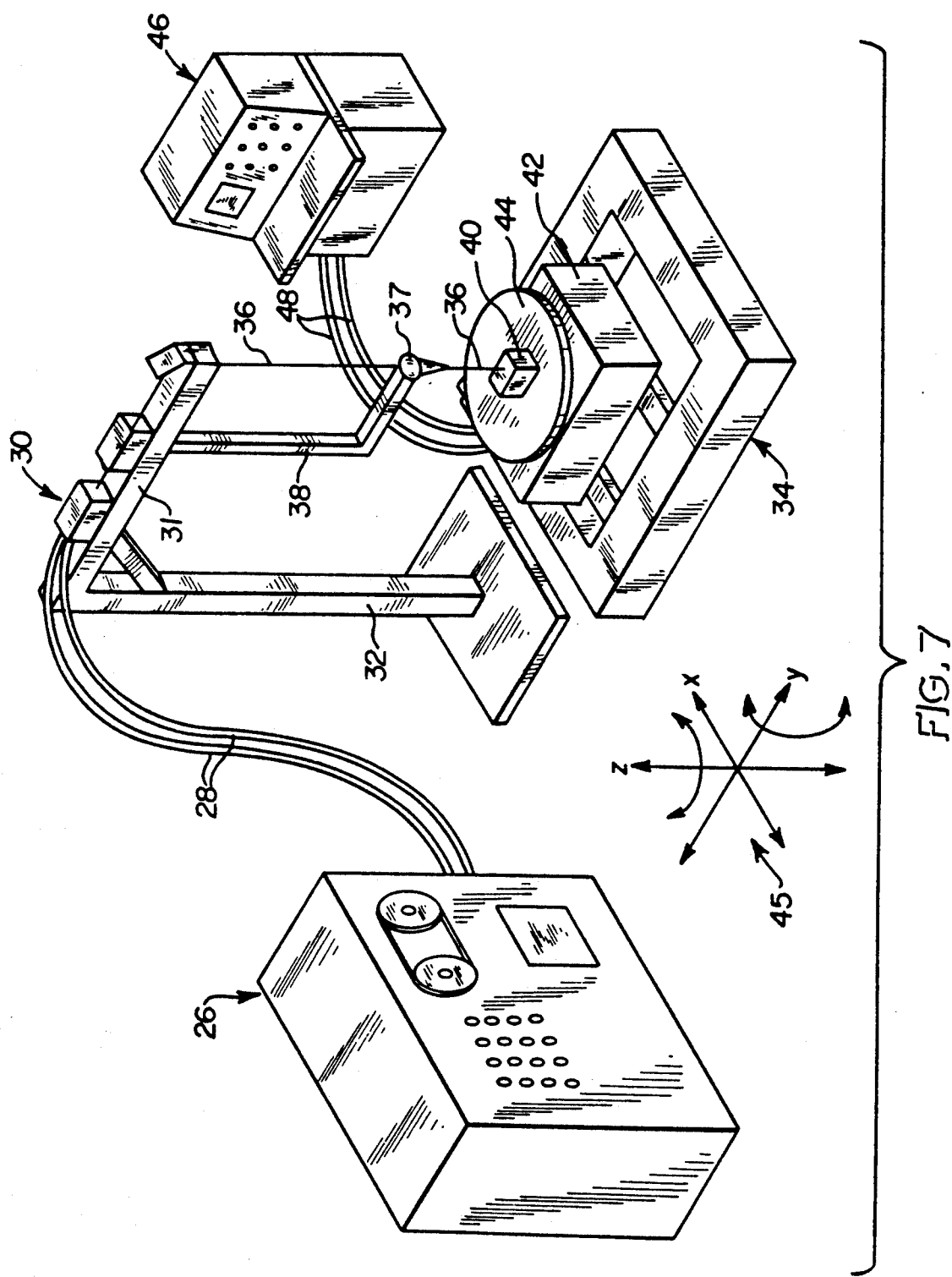
FIG. 7 is a schematic perspective view of a laser device and workpiece positioning table and associated controls useful in practicing a method of the present invention.

In FIGS. 1 and 2, a thin workpiece 2 is depicted in idealized fashion having a flat upper surface 4 and a plurality of pores or cavities 6 drilled therein by means of a laser device such as that schematically shown in FIG. 7. Of course, it is understood that the scale of FIGS. 1 and 2 is enlarged approximately 10 times actual size so that the details of the cavities 6 can be easily seen. Utilizing a pulsed laser beam with a controlled energy level, the cavities 6 are formed in the surface 4 of the workpiece 2 in a repetitive manner as shown in FIG. 1. Typically, the operating conditions are selected such that the cavities 6 have a controlled depth "a" which is less than the thickness of the workpiece 2 so as to avoid complete penetration thereof. A typical overall thickness of the workpiece 2 may be on the order of about $\frac{1}{8}$". The cavity diameter "d" is likewise controlled as well as the cavity spacing "s" such that bone ingrowth and bone cement adherence is enhanced.

EXAMPLE 1

A flat titanium workpiece of "CP" or commercially pure titanium was prepared having a planar surface 4 as in FIGS. 1 and 2. The titanium substrate 2 was positioned on a moveable work table spaced from a YAG laser. The alignment of the workpiece 2 was calibrated using a red ruby laser alignment beam produced by the laser machine in conventional fashion. After aligning the laser focusing lens approximately 5" from the titanium substrate 2, a shielding or inert cover gas of argon was turned on and the YAG laser was activated in a pulsating mode having a frequency of approximately 11 pulses per second. The table with the CP titanium substrate 2 mounted thereon was moved beneath the stationary pulsating laser beam and a series of cavities 6 were formed therein along a first row "A", FIG. 1. The table and attached workpiece were moved at a constant rate; the laser, which also was pulsed at a constant frequency, formed cavities 6 in an equally spaced manner. Rather than moving at a constant rate, the table and workpiece can be intermittently moved. After the row "A" of cavities 6 was formed, the laser was turned off and the table returned to the starting position and indexed one cavity spacing "s" perpendicular to the first row "A" of the newly produced cavities. At this point, a second row "B" of cavities was formed. This procedure of row indexing was repeated for rows "C" through "H" until the desired modified area of surface porosity was produced. A typical diameter "d" for the cavities 6 is between about 0.020" and about 0.030", with a preferred depth "a" between about 0.020" and 0.030" and a center-to-center cavity spacing "s" of between about 0.025" and 0.030". A preferred range for the cavity spacing is greater than $\frac{1}{2}$ a cavity diameter, but preferably less than 0.125".

Figure 5:
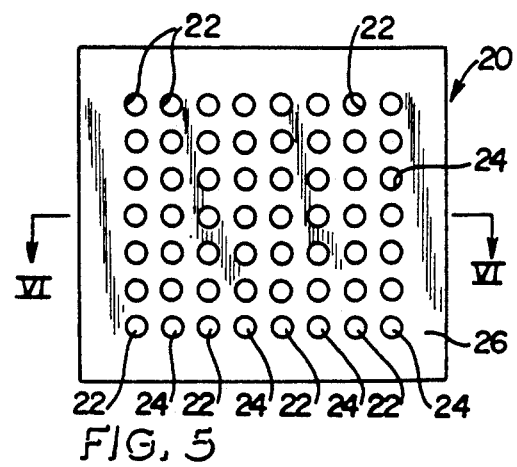
FIG. 5 is an enlarged plan view of a porous surface in accordance with the present invention.
Figure 6:
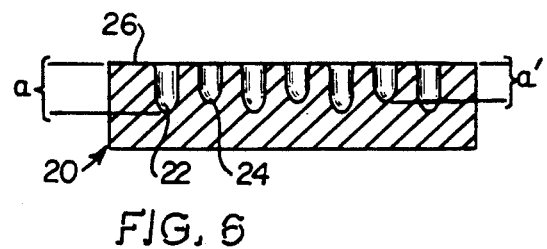
FIG. 6 is a cross-sectional side view of the surface taken along line VI—VI of FIG. 5.

As seen in FIGS. 5 and 6, the rows of cavities 22 and 24 may be formed of different depths a, a' to provide a porous surface of varying yet controlled porosity across a predetermined width thereof. In this example, depth a is about 0.020" and a, is about 0.030".

Figure 8A:
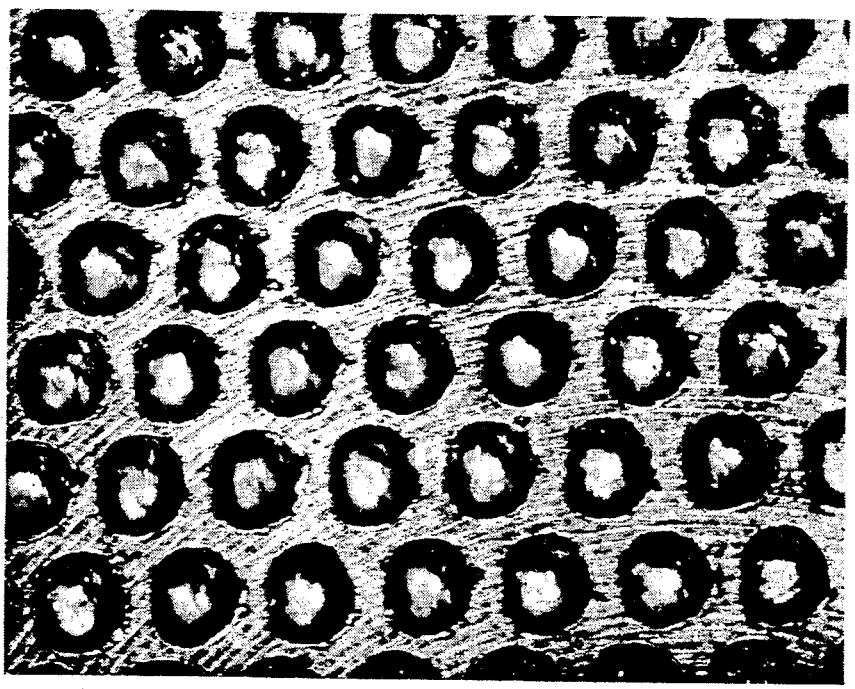
FIG. 8A is a photomicrograph of a cobalt-chromium alloy showing a porous surface produced in accordance with the present invention at a magnification of 20 power.
Figure 8:
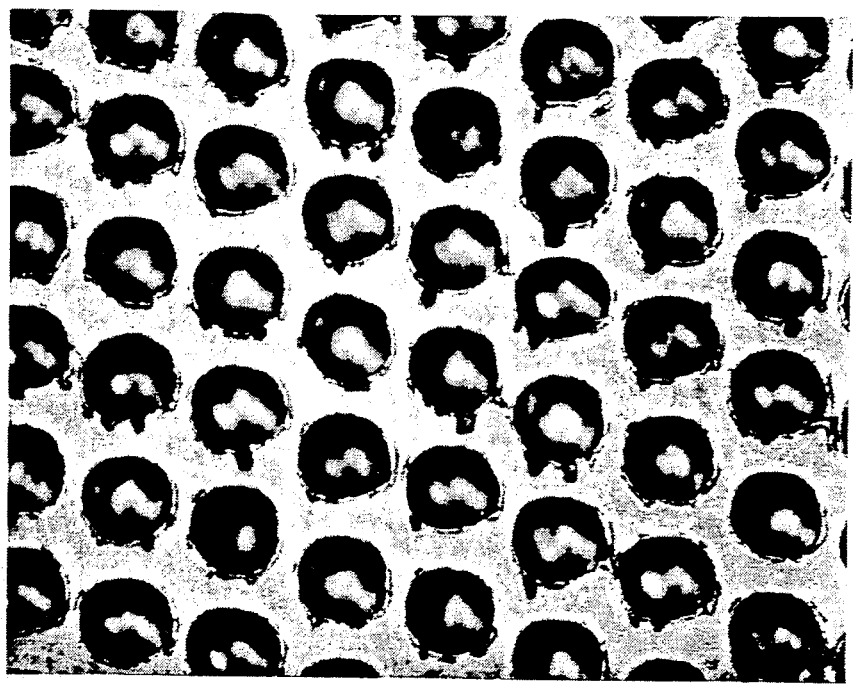
FIG. 8 is a photomicrograph of a titanium alloy workpiece showing a porous surface produced in accordance with the present invention at a magnification of 20 power.
Figure 9:
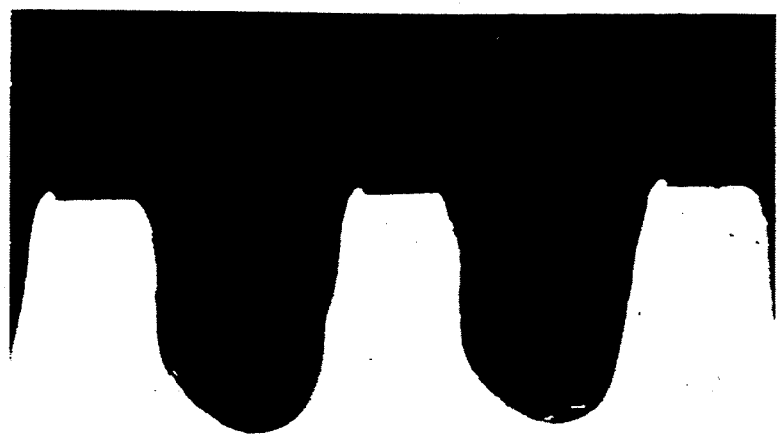
FIG. 9 is a photomicrograph showing a cross-sectional side view of two cavities in a titanium alloy workpiece at a magnification of 50 power.
Figure 10:
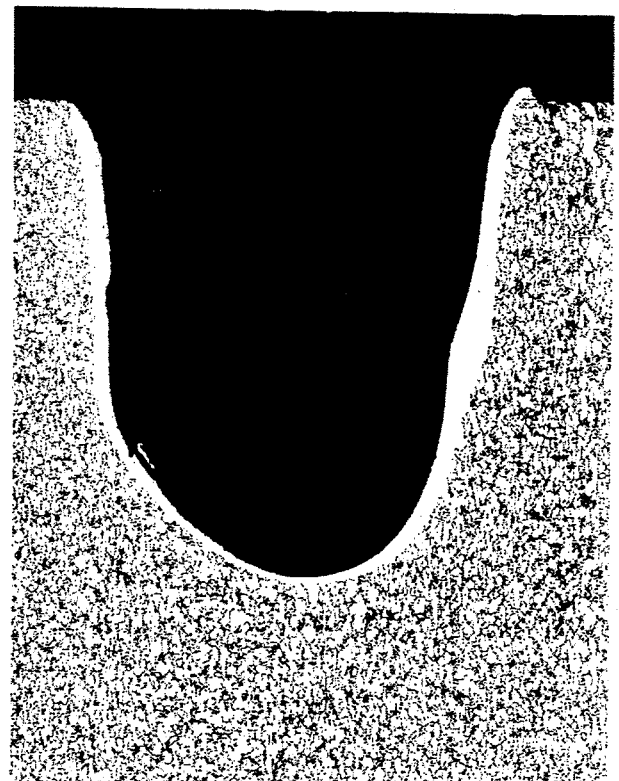
FIG. 10 is a photomicrograph showing a cross-sectional view of a cavity formed in a titanium alloy at 100 power magnification.

Photomicrographs of actual porous surfaces and individual cavities formed by the invention are depicted in FIGS. 8, 8A, 9 and 10. It will be readily observed from the photomicrographs that a typical cross-sectional cavity geometry is not completely concentric as indicated in FIGS. 1, 2, 5 and 6 of the drawings. Rather, the cavities are slightly skewed from the vertical axes in the direction of the travel direction of the positioning table. This slightly skewed configuration is actually beneficial in that it presents a greater opportunity for stronger mechanical bonding between the cement and/or bone structure and the implant than is the case with a smooth, concentrically formed cavity surface. The small melted and frozen protrusions at the top surface of the cavities can also be readily removed for cosmetic purposes through a simple tumbling operation after the laser drilling step is completed. The photomicrographs of FIGS. 8, 9 and 10 show a plurality of cavities having a diameter of about 0.024", a depth of about 0.025", with a spacing of about 0.030" from cavity center to cavity center.

EXAMPLE 2

Figure 4A:
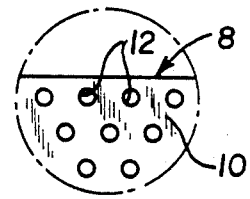
FIG. 4A is an enlarged view of a portion of the porous surface taken from area 4A of FIG. 4.
Figure 4:
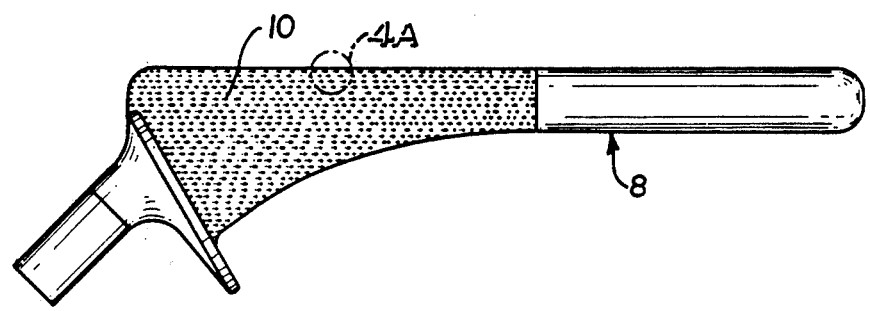
FIG. 4 is a side elevation view of a hip prosthetic device having a pattern of surface porosity produced in accordance with the present invention.

A femoral stem of a hip prosthesis 8 constructed, for example, of a Titanium-6 Aluminum-4 Vanadium ELI alloy is depicted in FIG. 4 having a porous surface portion 10 formed in accordance with the present invention. The pore pattern 10, as seen in FIG. 4A, is triangular in plan view configuration and was applied to selected areas to enhance bone ingrowth on the anterior and posterior surfaces of the implantable device 8. As seen in the actual photomicrographs of FIGS. 8 and 9, and in FIG. 4A, cavities 12 were formed in surface 10 having a diameter of 0.024" and a depth of 0.025" with a center-to-center cavity spacing of 0.030" average. The cavities 12 were formed using a $CO_2$ laser with an argon cover gas to protect the surface of the oxygen reactive titanium alloy during the laser drilling operation.

Figure 3:
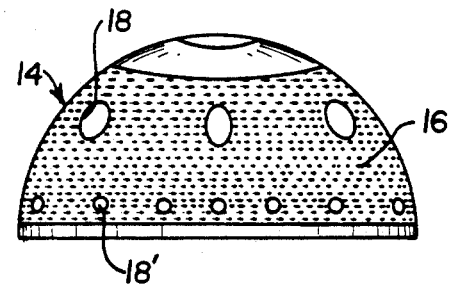
FIG. 3 is a side elevation view of an acetabular cup having a porous surface formed in accordance with the present invention.

Curved or other complex surface geometries may also be utilized in the method of the invention. As seen in FIG. 3, an acetabular hip cup 14 in the shape of a thin-walled hemisphere has its outer surface treated according to the present invention wherein a porous surface 16 is formed around a selected portion thereof. A typical acetabular hip cup 14 includes spaced screw holes 18, 18' formed therein for securement of screws directly to the bone. The cup 14 possesses a thin wall, on the order of about 0.125" thick, which makes laser drilling of the cavities to a controlled depth of about 0.030" particularly desirable. In this manner, a porous surface 16 of controlled depth is formed on the outer surface of the cup 14 without drilling through the thin wall and without impairing the load bearing structural integrity of the cup. The danger of tissue contamination potentially present in prior art porous surface coating techniques is, likewise, eliminated.

Figure 11:
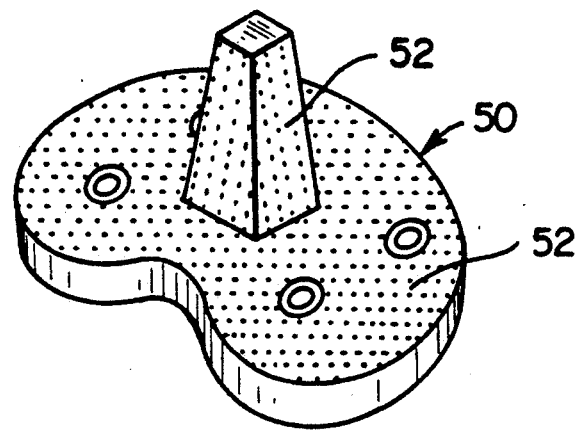
FIG. 11 is a top side perspective view of a tibial knee tray useful in a knee implant system.
Figure 12:
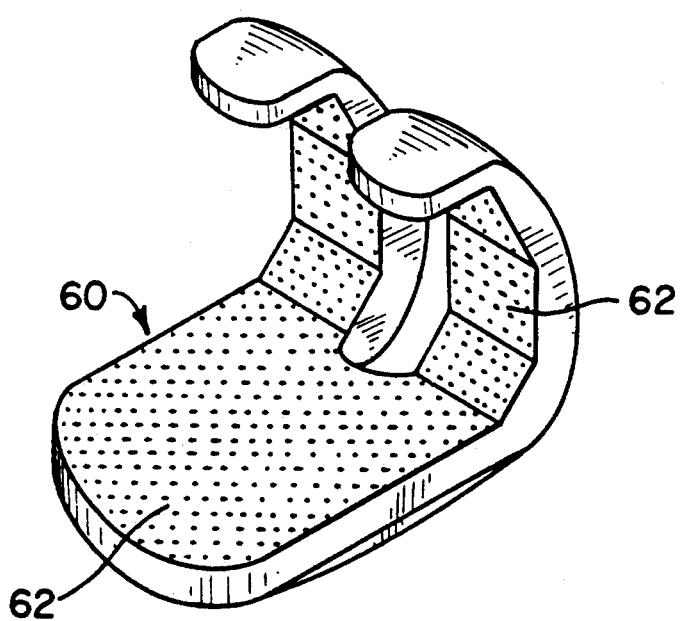
FIG. 12 is a top side perspective view of a femoral knee component useful in a knee implant system.

Examples of other complex surface geometries are shown in FIGS. 11 and 12. A tibial knee tray 50 having a porous surface 52 formed in accordance with the invention is shown in FIG. 11. A femoral knee component 60 having a porous surface 62 formed in accordance with the present invention is depicted in FIG. 12. The femoral knee component 60 and the tibial knee tray 50 are useful components in a knee implant system.

EXAMPLE 3

A substrate 20 of a cobalt-chromium medical implant alloy designated ASTM F-75-87 was treated in accordance with the present invention. The cobalt-chromium alloy workpiece was positioned on a moveable work table spaced from a YAG laser and rows of cavities were formed in the surface thereof. FIG. 8A depicts a photomicrograph of the cobalt-chromium medical implant alloy at 20 power magnification showing controlled porosity produced with the YAG laser beam. The cavities are typically 0.027" in diameter and 0.021" average depth with a center-to-center spacing of about 0.030". The ASTM type F-75-87 cobalt-chromium alloy is a cast material and it is understood that the wrought cobalt-chromium alloy designated ASTM F-799-87 is also suitable.

A single cavity formed in a Titanium-6 Aluminum-4 Vanadium ELI alloy is depicted in the photomicrograph of FIG. 10, at a 100 power magnification. It is observed in FIG. 10 that the laser drilling technique of the present invention utilizing a quickly pulsed beam produces a very thin heat affected zone surrounding each cavity. The heat affected zone is shown as a white layer in the photomicrograph, with the balance of the micro structure unaffected by the highly localized melting effected by the pulsed laser beam. Thus, the metallurgical structure and mechanical properties of the adjacent titanium alloy material are substantially unaffected by the laser drilling technique of the present invention.

One presently preferred arrangement of the basic equipment for practicing the method of the present invention is depicted in FIG. 7. A conventional laser electrical control system 26 for regulating the power and pulse frequency of the laser beam is operably coupled by conduits 28 to a conventional laser beam generator 30. The laser beam generator 30 is mounted on a cross brace 31 carried by a support stand 32 to position the laser beam generator in a spaced location above a workpiece positioning unit 34. The laser beam generator 30 is conventional and may include a YAG, $CO_2$, or like laser source for producing a coherent laser beam 36 useful for causing localized melting in metal or other materials. A conventional lens 37 is mounted on an arm 38 carried by the cross brace 31 for focusing the laser beam 36 on a surface of a workpiece 40, such as the medical implant acetabular cup 14 or femoral stem 8, as previously described.

The workpiece positioning unit 34 includes a moveable work table 42 carrying a rotatable platen 44 which together are moveable in the three x, y and z axes and rotatable about the y and z axes, as shown in the representation of the x, y and z axes identified by reference numeral 45 in FIG. 7. In this manner, the work positioning unit 34 provides five degrees of freedom for positioning the workpiece 40 relative to the laser beam 36 whereby surfaces of any contour can be treated in accordance with the invention. Movement of the workpiece positioning unit 42 is controlled by a conventional numerical controlled or "NC" positioning system control 46 of the type commonly used in the computer controlled machine tool art. The positioning system control 46 is operably coupled to the workpiece positioning unit 42 by way of conduits 48. Through appropriate programming of the positioning system control 46, the workpiece 40 is moved a proper distance and/or at a proper speed relative to the pulse rate of the laser beam 36 controlled by the laser control system 26 to provide proper spacing between the cavities formed in the workpiece 40 by the laser beam 36. Likewise, when drilling non-planar surfaces, a proper focal length is maintained by vertical movement of the workpiece positioning unit effected by the pre-programmed commands supplied by the positioning system control 46 which also controls the horizontal indexing movement of the workpiece positioning unit 34. As a result, high quality and consistent dimensional accuracy is assured.

Of course, it is understood that the workpiece can remain stationary and the laser beam generator 30 can be moved to accomplish similar results. Also, while the invention has been described in connection with only one laser beam, it will occur to those skilled in the art that multiple laser beams could be employed simultaneously to form a porous surface according to the invention.

EXAMPLE 4

Modified Cavity Shapes

Figure 13:
FIG. 13 is a photomicrograph at 50X magnification of a cross section of a laser drilled conically shaped cavity.

The above described laser drilling techniques provide drilled cavities which are generally cylindrical in shape with a radiused bottom. It has been found that changes in the operational parameters of the laser enable the formation of various cavity shapes and geometries. Shapes ranging from conical to "bulbous" have been produced. FIG. 13 shows a cross section of a conical cavity drilled with a Nd: YAG laser. The conical cavity shape is obtained by using a very short laser beam pulse duration, on the order of about 0.3 milliseconds. Combining this short duration pulse with higher average power levels, for example 150 to 230W, enables cavities to be drilled at rates up to 100 cavities per second. Obviously this translates into a substantial improvement in the economics of the process. In addition, a conical shaped cavity offers the advantage of less material being removed from the workpiece which, thus, yields a potentially stronger implant.

Figure 14:
FIG. 14 is a photomicrograph at 50X magnification of a cross section of a laser drilled cavity having a bulbous shape.

A further cavity shape is shown in FIG. 14. This particular cavity geometry is referred to as a "bulbous" shape because the drilled hole is actually wider beneath the surface than it is at the surface. When an implant device containing this surface cavity geometry is implanted into the body, bone tissue can grow into these bulbous holes, thus, creating an effective mechanical interlock. A similarly enhanced interlock would be created if conventional bone cement was used with the bulbous holes. The bulbous shaped cavities were produced by using a Nd: YAG laser resonator which produces pulses of energy of longer duration and lower intensity. Pulse duration of 0.5 milliseconds at an average power of 30–50 watts produced 5 cavities/second.

EXAMPLE 5

Angled Cavities

Typically, as described above, laser drilled cavities are oriented perpendicular to the workpiece surface, as shown in FIG. 2. Since most loading at an implant-bone interface is in shear, the bone which grows into such perpendicular holes will also be loaded in shear. Because most materials can sustain the least load in shear, it would be desirable to alter the stress at this interface. Laser drilling of the cavities at an angle to the surface of the implant enables the pure shear loading to be altered to include a compressive component. This is accomplished by tilting one or both of the laser 30 or the workpiece 40 during drilling, FIG. 7. The orientation of the angled cavities can be selected to maximize the benefit depending upon the loading expected in a particular area of an implant. In fact, the orientation, as well as the angle, can be adjusted for various parts of the implant. Further, subsequent rows of cavities may be produced at different orientations to enhance the interlocking of the bone and implant. In addition, the angled bone to transfer tensile forces to the implant and resist pulling out of the cavity.

Figure 15:
FIG. 15 is a photomicrograph at 50X magnification of a cross section of an angularly drilled cavity.
Figure 16:
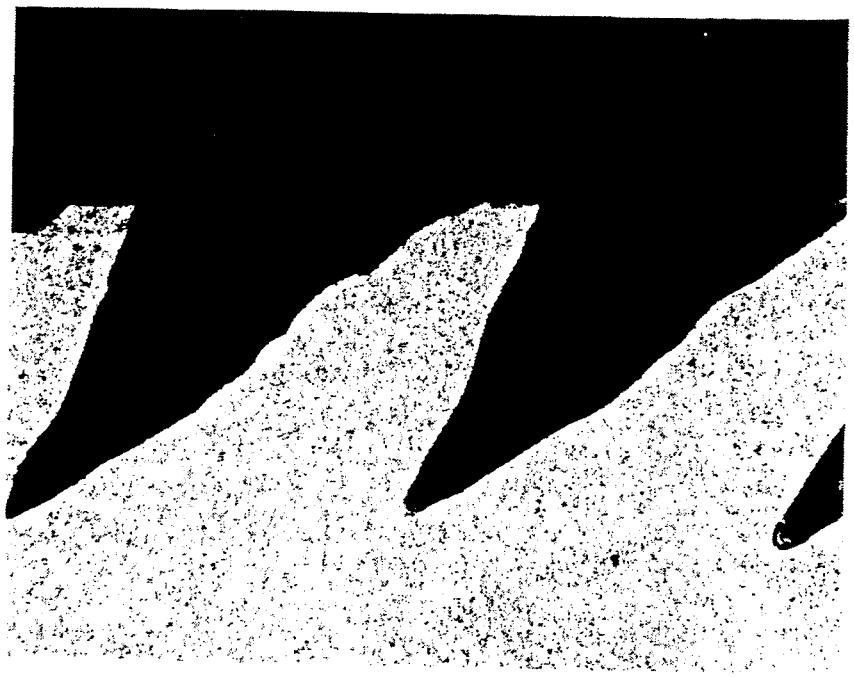
FIG. 16 is a photomicrograph also at 50X magnification similar to the cross section of FIG. 15 but at a decreased angle.

The angle of the cavities to the part surface can be as low as 10°. By way of example, FIGS. 15 and 16 show cavities which have been drilled at 20° and 45° relative to the surface, respectively.

EXAMPLE 6 Roughened Surfaces

Figure 17:
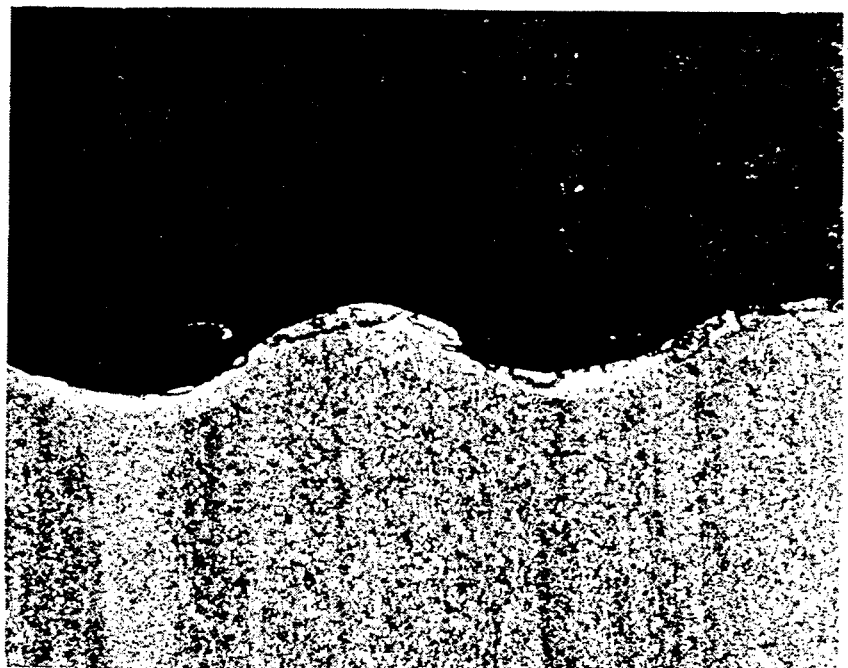
FIG. 17 is a photomicrograph at 50X magnification of a cross section of a workpiece surface roughened by laser treatment in accordance with the invention.

While the laser drilled cavities provide definite benefits, there is one drawback. Each cavity that is drilled obviously removes a quantity of metal from the part and, therefore, reduces the load carrying cross section. This reduction in area is not significant on larger parts; however, smaller parts typically have less of a safety factor and any reduction in load carrying capacity is cause for concern. A variation of the laser drilled surface has been created by modifying the laser parameters, principally by defocussing the laser beam. This surface does not contain well defined or distinct holes, but rather consists of dimples and resolidified metal but represents an increased surface area over an untreated surface. It is more accurately described as a "roughened surface". FIG. 17 shows a cross section of this roughened surface. The laser parameters used to generate a typical roughened surface requires, for example, an average power of 220 watts, a pulse duration of 0.3 milliseconds and 35 pulses per second. A 76.2 mm focal length lens was used and was defocussed by 0.225 inch to produce the roughened surface shown in FIG. 17.

EXAMPLE 7

Bone Growth Stimulants

A further enhancement provided by the laser drilled surface is its function as a firm base or foundation for depositing materials which act as bone growth stimulants and/or medications. Known bone growth stimulants consist primarily or hydroxylapatite, tricalcium phosphate and bone growth factor. Certain antibiotic medications may also be applied. Typically, in the prior art, these materials are applied in paste form directly to a smooth surfaced implant by the medical personnel at the time of surgery. The characteristics of these materials have been shown to accelerate the growth of bone in the local regions. Because of the physical properties of the bone growth stimulant coatings, they are particularly susceptible to failure by shearing away from smooth metal surface.

Utilizing the previously described laser drilled surfaces, as well as the roughened surface described in Example 6, creates additional surface area for the bone growth stimulant coatings to adhere. Also, the irregular nature of the laser treated surfaces protects the coatings from direct shear loads, thus eliminating a major drawback to the use of these coatings.

The laser treated implant devices of the present invention may be coated with the bone growth stimulant paste mixture by the medical team performing the implant surgery or the device may be precoated with a bone growth stimulant prior to shipment. The laser treated surface can receive a coating of hydroxylapatite and tricalcium phosphate by plasma spray deposition. The hydroxylapatite and tricalcium phosphate compounds are ceramic materials which may be introduced to the plasma spray as a fine powder which quickly becomes molten prior to deposition on the laser treated surface of the implant device. The solidified and cooled coating of bone growth stimulant material is then handled in normal fashion due to its rather hard condition after spraying, and due to its strong mechanical adherence to the laser drilled cavities and/or laser roughened surface area. The laser sprayed hydroxylapatite and tricalcium phosphate coating remains substantially chemically inert until it is implanted, at which time a bone growth factor may be applied to the surface along with medication by the medical personnel. It is also noted that the pre-applied, plasma sprayed coating offers superior cavity penetration over the manual application of hydroxylapatite and tricalcium phosphate in paste form. It will, thus, be readily appreciated by those skilled in the art that the precoated implant device of the present invention offers a convenient and timesaving advance over prior devices.

EXAMPLE 8

Release Agents

During laser drilling, the interaction of the laser beam and the workpiece metal results in a portion of the material vaporizing while some merely melts. The molten metal redeposits as fine particles or "splatter" on the surface of the workpiece. Since an inert assist gas, usually argon, is used, the molten material retains its metallic characteristics. Upon contacting the metal part, the splattered particles resolidify and adhere very tightly. These particles are not acceptable on an implant due to the possibility that they will detach once the workpiece is implanted, causing serious problems afterwards.

In order to avoid these problems, the surfaces to be laser drilled are coated with a release agent to prevent the molten metal particles from tightly bonding to the metal implant. The release agent must not prevent the laser energy from coupling with the metal, but it must be stable at high temperatures. Refractory materials such a $Y_2O_3$, $Al_2O_3$, BN, MgO, $TiO_2$, graphite and other high temperature materials are suitable. Typically, the release agent is prepared as a slurry and applied to the part, preferably by spraying. Brushing or dipping, as well as other known techniques, may be utilized. As the part is laser drilled, the molten metal particles solidify on the coating of release agent and do not contact the metal surface. The release agent and the splattered particles are easily removed by washing the part with water. Brushing and ultrasonic agitation may also be used to assist in the cleaning. The exact cleaning method is dictated by the nature of the binders in the release agent which will be readily apparent to those skilled in the art of metal cleaning.

Figure 18:
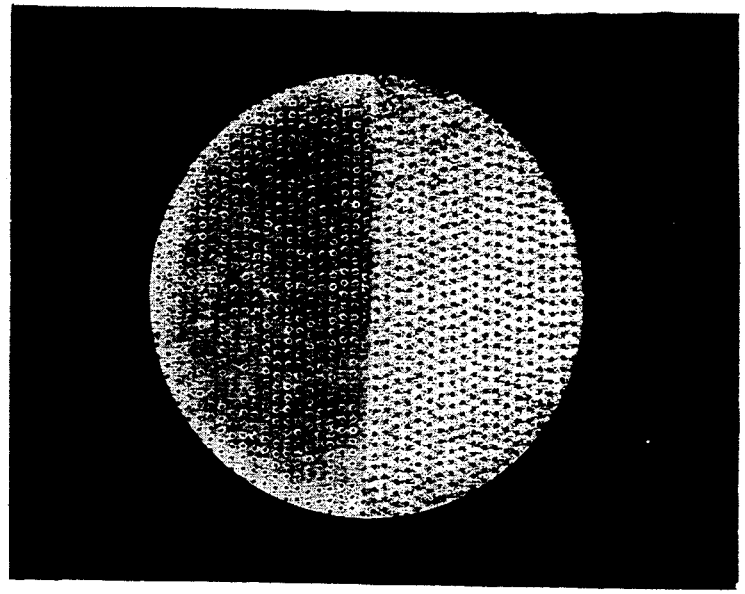
FIG. 18 is a photomicrograph at 1.5X magnification in plan view of a sample disc after laser drilling and washing, the disc had a boron nitride coating applied to the left side prior to laser drilling.
Figure 19:
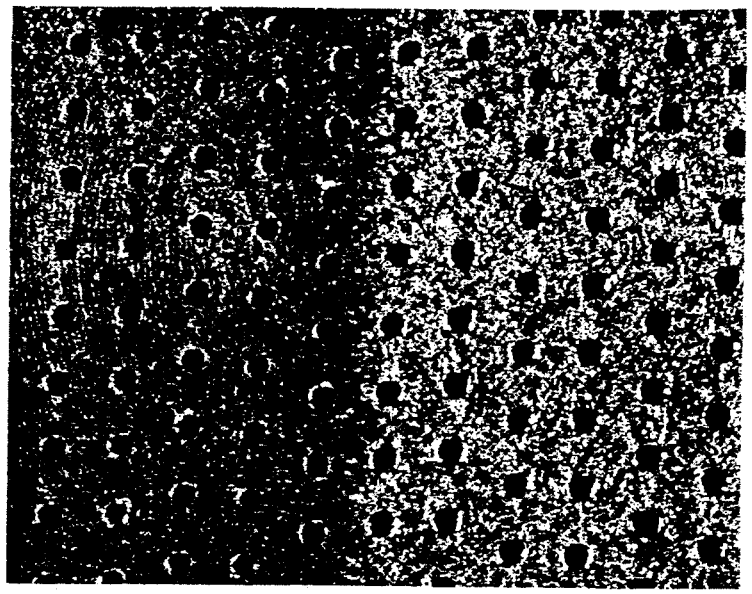
FIG. 19 is a photomicrograph at 10X magnification in plan view of the sample disc of FIG. 18 taken along the interface between the boron nitride coated and uncoated surfaces.
Figure 20:
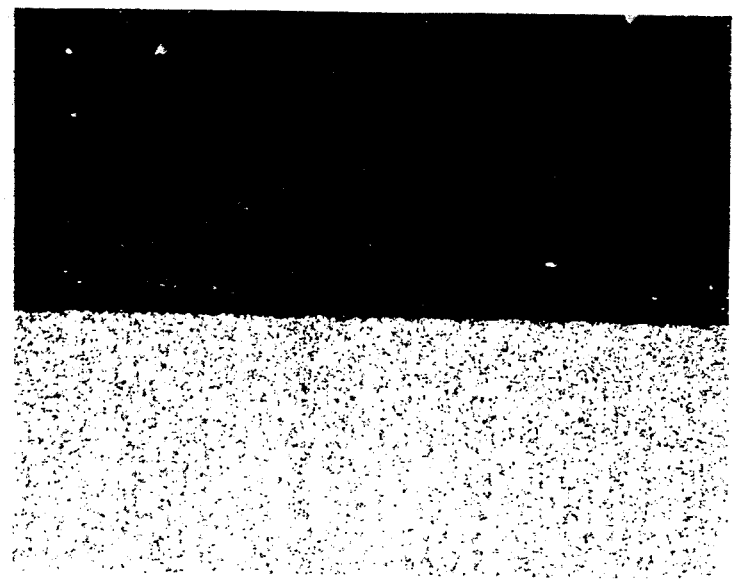
FIG. 20 is a photomicrograph at 100X magnification of a cross section of the laser processed disc or FIGS. 18-19 taken along the surface of the boron nitride coated area.
Figure 21:
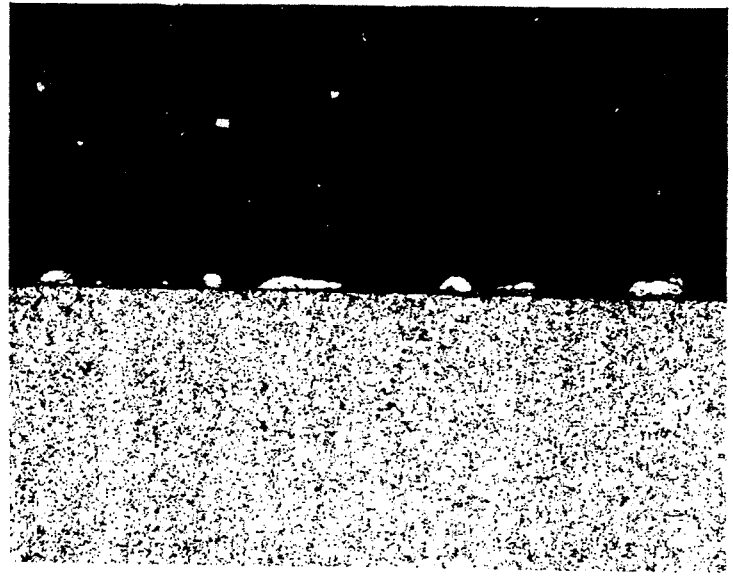
FIG. 21 is a photomicrograph at 100X magnification similar to FIG. 20 but taken along the uncoated surface showing molten metal splatter thereon.

In order to demonstrate the effectiveness of the boron nitride coating, a sample disk of Ti67Al-4V ELI metal alloy was coated on the left half of its surface with boron nitride (BN). The disk was then laser processed with holes drilled 0.050 inch apart. The drilled disk was then washed in warm water and rubbed by hand resulting in the surface condition depicted in FIG. 18. FIG. 19 shows a magnified view of the BN coated and the uncoated surfaces. The remaining metallic splatter is quite evident on the uncoated surface appearing on the right side of the sample. The sample disk was then sectioned and examined under higher magnification. FIGS. 20 and 21 show the BN coated and uncoated surfaces, respectively. The absence of metal splatter in the BN coated surface of FIG. 20 is quite evident.

EXAMPLE 9

Chemical Maskants

On occasion, it is desirable to chemically etch the workpiece after the cavities are laser drilled. This etching treatment may be required to enlarge or modify the shape of the cavities, as well as to remove any splattered particles which might have fallen into and solidified within previously drilled holes. Merely submerging an as-drilled, unprotected workpiece in acid would result in material being removed from the cavities, but also from top surfaces between cavities. This is not desirable since the area between the cavities defines a tightly toleranced surface.

In order to overcome this problem, an acid resistant coating, typically a polymer, is applied to the workpiece. A release agent (described in Example 8) is also preferably applied over the maskant. Laser drilling is then performed as previously described. It is not necessary to remove the resolidified particles and release agents prior to etching, but such a removal step is recommended in order to maintain the cleanliness of the echant solution. Etching is performed in a solution whose composition is dependent upon the metal to be etched. For titanium and its alloys, for example, a solution of up to 20% hydrofluoric acid is used. Nitric acid may slowly be added but is not absolutely necessary. For cobalt based materials, solutions containing hydrochloric, acetic and chromic acids, as well as hydrogen peroxide and glycerol, may be used. Electrolytic etching of the workpiece may also be used in accordance with etching practices known in the art.

An acid resistant chemical maskant which may be used is one or more of the products sold under the trade designations: AC-818-T; AC-818-C; AC-872-1: AC-832-TC (Top Coat); marketed by AC Products, Inc. of Placentia, California. We employ a typical maskant coating thickness on the workpiece surface of about 0.002 inch.

having described presently preferred embodiments, it is to be understood that it may be otherwise embodied within the scope of the appended claims.

Having described the invention, what is claimed is:

1. A process for forming a porous surface on a metal implant device comprising the steps of:
    (a) providing a laser apparatus for generating a pulsed laser beam;
    (b) coating said metal implant device with a release agent;
    (c) activating said laser apparatus to form said porous surface; and
    (d) removing said release agent and accumulated metal platter from said implant device.

2. The process of claim 1 wherein the release agent comprises a refractory material selected from the group consisting of yttria, alumina, boron nitride, magnesia, titanium oxide and graphite.

3. The process of claim 1 wherein the release agent comprises a slurry containing boron nitride which is applied to said implant device in a coating having a thickness of between about 0.002 to about 0.003 inch.

4. A process for forming a porous surface on a metal implant device comprising the steps of:
    (a) providing a laser apparatus for generating a laser beam;
    (b) coating said metal implant device with a chemical maskant;
    (c) drilling a plurality of cavities in the metal implant device with said laser beam;
    (d) submerging said drilled device in an etching bath and etching said drilled cavities to selectively remove metal therefrom; and
    (e) cleaning said etched device to remove said chemical maskant therefrom.

5. The process of claim 4 wherein the etching step is one selected from the group consisting of chemical etching and electrolytic etching.

6. A process for forming a porous surface on a metal implant device comprising the steps of:
    (a) providing a laser apparatus for generating a pulsed laser beam;
    (b) coating said metal implant with a layer of a chemical maskant;
    (c) coating said layer of chemical maskant agent with a release agent;
    (d) pulsing said laser to drill a plurality of cavities in said coated metal implant device;
    (e) submerging said drilled and coated implant device in an etching bath and etching said drilled cavities to selectively remove metal therefrom; and
    (f) cleaning said etched implant device to remove said chemical maskant coating therefrom.

7. The process of claim 6 wherein the etching step is one selected from the group consisting of chemical etching and electrolytic etching.

8. The process of claim 6 including the step of applying a coating of bone growth stimulant to said porous surface after said cleaning step.

9. The process of claim 8 wherein said bone growth stimulant comprises a plasma sprayed coating of hydroxylapatite and tricalcium phosphate.

* * * * *

UNITED STATES PATENT AND TRADEMARK OFFICE
CERTIFICATE OF CORRECTION

PATENT NO. : 5,246,530                                Page 1 of 2

DATED : September 21, 1993

INVENTOR(S) : Clifford M. Bugle and Alfred L. Donlevy

It is certified that error appears in the above-indentified patent and that said Letters Patent is hereby corrected as shown below:

Column 2 Line 56 "crating" should read --creating--.

Column 3 Line 6 "to" (first occurrence) should read --in--.

Column 3 Lines 13-14 "supplied" should read --applied--.

Column 4 Line 26 "or" should read --of--.

Column 4 Line 36 "Will" should read --will--.

Column 6 Line 10 "a," should read --a'--.

Column 9 Line 13 after "angled" insert --cavities provide an effective undercut which will enable--.

Column 9 Line 21 begin a new line with "Roughened".

Column 9 Line 51 "or" should read --of--.

UNITED STATES PATENT AND TRADEMARK OFFICE
CERTIFICATE OF CORRECTION

PATENT NO. : 5,246,530

DATED : September 21, 1993

INVENTOR(S) : Clifford M. Bugle and Alfred L. Donlevy

It is certified that error appears in the above-indentified patent and that said Letters Patent is hereby corrected as shown below:

Column 9 Line 61 "surface." should read --surfaces.--.

Column 10 Line 65 "Ti67Al-4V" should read --Ti6Al-4V--.

Column 11 Line 38 "slowly" should read --also--.

Column 11 Line 46 "AC-872-1:" should read --AC-872-1;--.

Column 11 Line 52 "having" should read --Having--.

Claim 1(d) Line 8 Column 12 "platter" should read --splatter--.

Signed and Sealed this

Twenty-second Day of March, 1994

Attest:

BRUCE LEHMAN

Attesting Officer     Commissioner of Patents and Trademarks